US00PP12282P2

(12) United States Plant Patent
Osiecki

(10) Patent No.: US PP12,282 P2
(45) Date of Patent: Dec. 18, 2001

(54) SYNGONIUM PLANT NAMED 'GLO-GO'

(75) Inventor: Marian W. Osiecki, Marianna, FL (US)

(73) Assignee: Oglesby Plants Intl., Inc., Altha, FL (US)

( * ) Notice: Subject to any disclaimer, the term of this patent is extended or adjusted under 35 U.S.C. 154(b) by 0 days.

(21) Appl. No.: 09/561,017

(22) Filed: Apr. 28, 2000

(51) Int. Cl.[7] ..... A01H 5/00
(52) U.S. Cl. ..... Plt./374

(58) Field of Search ..... Plt./374, 373

*Primary Examiner*—Bruce R. Campell
*Assistant Examiner*—June Hwu
(74) *Attorney, Agent, or Firm*—C. A. Whealy

(57) ABSTRACT

A distinct cultivar of Syngonium plant named 'Glo-Go', characterized by its compact, dense, rounded, symmetrical and non-vining growth habit; relative high vigor; freely and early branching habit; and leaves with a striking, distinct, and well-defined greenish white pattern on a dark green background.

2 Drawing Sheets

BACKGROUND OF THE INVENTION

The present Invention relates to a new and distinct cultivar of Syngonium plant, botanically known as *Syngonium podophylum*, and hereinafter referred to by the cultivar name Glo-Go. The new Syngonium is a product of a mutation induction breeding program conducted by the Inventor in Altha, Fla. The objective of the program is to create new fast-growing Syngonium cultivars with compact and non-vining plant habit and attractive leaf coloration and pattern.

The new Syngonium originated by exposing unrooted cuttings of the Syngonium cultivar Robusta, not patented, to gamma-ray radiation from a Cobalt 60 source at the Florida Department of Agriculture and Consumer Services, Division of Plant Industry, in Gainesville, Fla., in the fall of 1993. Following the radiation treatment, the cuttings were rooted and plants grown in a controlled environment in Altha, Fla. The new Syngonium was discovered and selected after several selection cycles in September, 1994, by the Inventor as a single plant within this population. The selection of this plant was based on its plant habit, vigor, and attractive leaf coloration and pattern.

Asexual propagation of the new cultivar by tissue culture in Altha, Fla., has shown that the unique features of this new Syngonium plant are stable and reproduced true to type in successive generations of asexual propagation.

SUMMARY OF THE INVENTION

The new Syngonium has not been observed under all possible environmental conditions. The phenotype may vary somewhat with variations in environment such as temperature, light intensity, fertilizer rate, irrigation amount and frequency, and/or propagation procedures without, however, any variance in genotype.

The following traits have been repeatedly observed and are determined to be the unique characteristics of 'Glo-Go'. These characteristics in combination distinguish 'Glo-Go' as a new and distinct cultivar:

1. Plants of the new Syngonium have a compact, dense, rounded, symmetrical and non-vining growth habit.

2. Plants of the new Syngonium are relatively vigorous.

3. Plants of the new Syngonium are freely branching and begin branching early in their development.

4. Leaves of plants of the new Syngonium have a striking, distinct, and well-defined greenish white pattern on a dark green background. The proportion of greenish white to dark green background coloration decreases as plants of the new Syngonium mature.

Plants of the new Syngonium differ from plants of the parent cultivar Robusta in the following characteristics:

1. Plants of the new Syngonium are fuller, more compact and more symmetrical in growth habit than plants of the cultivar Robusta.

2. Plants of the cultivar Robusta are vining in habit whereas plants of the new Syngonium are not vining in habit.

3. Plants of the new Syngonium are slightly less vigorous than plants of the cultivar Robusta.

4. Plants of the new Syngonium develop branches earlier and are more freely branching than plants of the cultivar Robusta.

5. Leaves of plants of the new Syngonium have a more striking and distinct greenish white pattern than leaves of plants of the cultivar Robusta.

Plants of the new Syngonium can be compared to the Syngonium cultivar White Butterfly, not patented. However, in side-by-side comparisons conducted in Altha, Fla., plants of the new Syngonium differ from plants of the cultivar White Butterfly in the following characteristics:

1. Plants of the new Syngonium are fuller, more compact and more symmetrical in growth habit than plants of the cultivar White Butterfly.

2. Plants of the cultivar White Butterfly are vining in habit whereas plants of the new Syngonium are not vining in habit.

3. Plants of the new Syngonium are less vigorous than plants of the cultivar White Butterfly.

4. Plants of the new Syngonium develop branches earlier and are more freely branching than plants of the cultivar White Butterfly.

5. Leaves of plants of the new Syngonium are darker green and have a more striking and distinct greenish white pattern than leaves of plants of the cultivar White Butterfly.

6. Plants of the new Syngonium have thicker petioles than plants of the cultivar White Butterfly.

Plants of the new Syngonium can be compared to the Syngonium cultivar Pixie, not patented. However, in side-by-side comparisons conducted in Altha, Fla., plants of the new Syngonium differ from plants of the cultivar Pixie in the following characteristics:

1. Plants of the new Syngonium are broader and more vigorous and have a more rapid growth rate than plants of the cultivar Pixie.

2. Leaves of plants of the new Syngonium are larger than leaves of the cultivar Pixie. In addition, leaves of plants of the new Syngonium have longer, non-overlapping lobes, whereas leaf lobes of plants of the cultivar Pixie often overlap.

3. Leaves of plants of the new Syngonium have a more striking and distinct greenish white pattern than leaves of plants of the cultivar Pixie.

4. Plants of the new Syngonium have thicker petioles than plants of the cultivar Pixie.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Syngonium.

The photograph on the first sheet comprises a top perspective view of a typical plant of 'Glo-Go' in a 15-cm container about 10 months after planting a single tissue culture-produced microcutting.

The photograph on the second sheet comprises a close-up view of the upper surfaces of typical leaves at different stages of plant development, youngest to oldest, left to right. The proportion of greenish white to dark green leaf coloration decreases with subsequent development of the plants.

DETAILED BOTANICAL DESCRIPTION

The following observations and measurements were recorded during the summer on plants grown in Altha, Fla. in polycarbonate-covered greenhouses and under conditions which closely approximate those used in commercial horticultural practice. During the production of these plants, day temperatures ranged from 25 to 32° C., night temperatures ranged from 22 to 27° C., and light level ranged from 800 to 2,000 foot-candles. Plants used for this description were grown as single plants in 15-cm containers and were about 9.5 months from planting a tissue culture-produced microcutting. Older plants may differ in some morphological characteristics such as leaf coloration and pattern. Fully developed plant structures and organs were used for the following observations and measurements unless otherwise indicated.

In the following description, color references are made to The Royal Horticultural Society Colour Chart except where general terms of ordinary dictionary significance are used. Numerical measurements represent averages from typical plants of 'Glo-Go'.

Botanical classification: *Syngonium podophyllum* cultivar Glo-Go.

Parentage: Induced mutation of *Syngonium podophyllum* cultivar Robusta, not patented.

Propagation:

*Type.*—By tissue culture.

*Time to initiate roots.*—Summer: About 21 days with 25 to 30° C. soil temperatures. Winter: About 28 days with 22 to 27° C. soil temperatures.

*Time to develop roots.*—Summer: About 13 to 14 weeks with 25 to 30° C. soil temperatures. Winter: About 15 to 16 weeks with 22 to 27° C. soil temperatures.

*Rooting characteristics.*—Thick primary roots with abundant fine lateral roots.

Plant description:

*Growth habit.*—Compact, dense, rounded, symmetrical and non-vining growth habit. Appropriate for 10 to 25-cm containers.

*Plant height.*—About 22.2 cm from soil level to top of leaf canopy.

*Plant diameter* (*area of spread*).—About 45.8 cm.

*Plant vigor.*—Vigorous, relatively rapid growth rate.

*Crop time.*—About five to six months are required to produce a finished plant in a 10-cm container from a single tissue culture-produced microcutting. About seven to eight months are required to produce a finished plant in a 15-cm container from a single tissue culture-produced microcutting.

*Leaf blade.*—Shape: Sagittate. Apex: Acuminate with cuspidate tendencies; sometimes twisted. Base: Sagittate, sometimes with some hastate tendencies; asymmetrical; deep lobing, lobes narrowly rounded to pointed, not overlapping. Leaves from young plants have more rounded lobes and bases with some cordate tendencies. Margin: Entire, slightly wavy. Length, mature leaves (leaf apex to end of longer lobe): About 13.6 cm. Lobe length, mature leaves (petiole to end of longer lobe): About 5.5 cm. Width, mature leaves (at petiole): About 7.7 cm. Length to width ratio, mature leaves: About 1.8 to 1. Aspect: Horizontal to slightly slanted downward. Texture/surface, both surfaces: Glabrous; slightly wavy; dull; young leaves slightly glossy. Color: Young leaves, upper surface: Darker green than 144A to lighter than 147A; bands of color close to 145D along darker veins. Few flecks similar and close to 145C to 145D scattered in green areas. Young leaves, lower surface: Slightly lighter than 147B; veins close to 144B to 144C. Mature leaves, upper surface: Background, dark green, 147A, or slightly lighter than 147A. Contrasting, well-defined, almost linear pattern along the darker veins, between 196D (greyed-green) and greenish white, 157B and 157C. Some flecks of the same color scattered in green areas. Proportion of greenish white to dark green coloration decreases with subsequent development. Leaves produced by young plants have proportionally wider and less regular areas of greenish white and may be predominately greenish white. Leaves produced by plants older than those used for this description have predominantly dark green leaves with greenish white coloration limited to the narrow bands along the veins. Mature leaves, lower surface: 147B; midrib slightly lighter than 147B; other primary veins, close to 144A to 144B.

*Petiole.*—Length: About 16 cm. Diameter, just below leaf blade: About 3.6 mm. Diameter, just above winged area: About 4.3 mm. Petiole wings, length: About 5.5 cm. Petiole wings, width: About 4.5 mm. Texture, both surfaces: Smooth. Color: Young leaves: Between 148A, 147B and 146B. Mature leaves, winged area: 148A to 148B flushed with a color similar to 174A. Mature leaves, above winged area: Close to or darker than 147B.

Inflorescence description: Inflorescence development not observed.

Disease/insect resistance: Plants of the new Syngonium grown in commercial greenhouses have not shown any unusual susceptibility to pathogens or insects common to Syngonium.

It is claimed:

1. A new and distinct cultivar of Syngonium plant named 'Glo-Go', as illustrated and described.

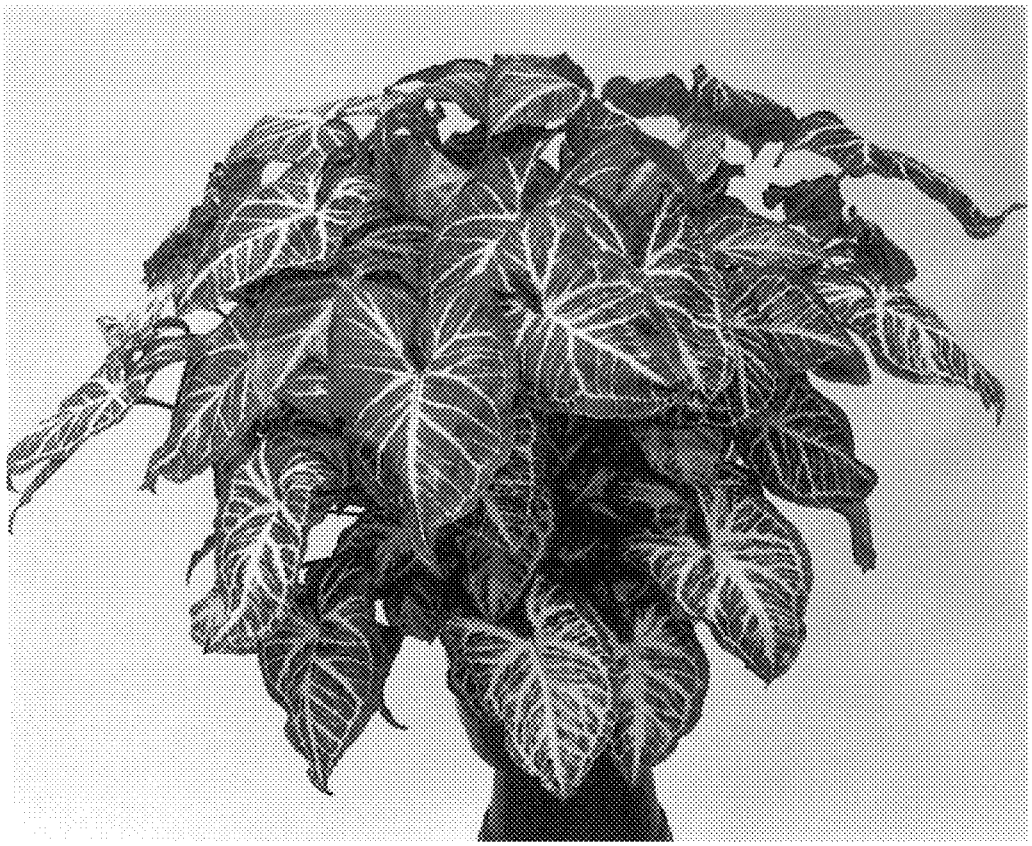

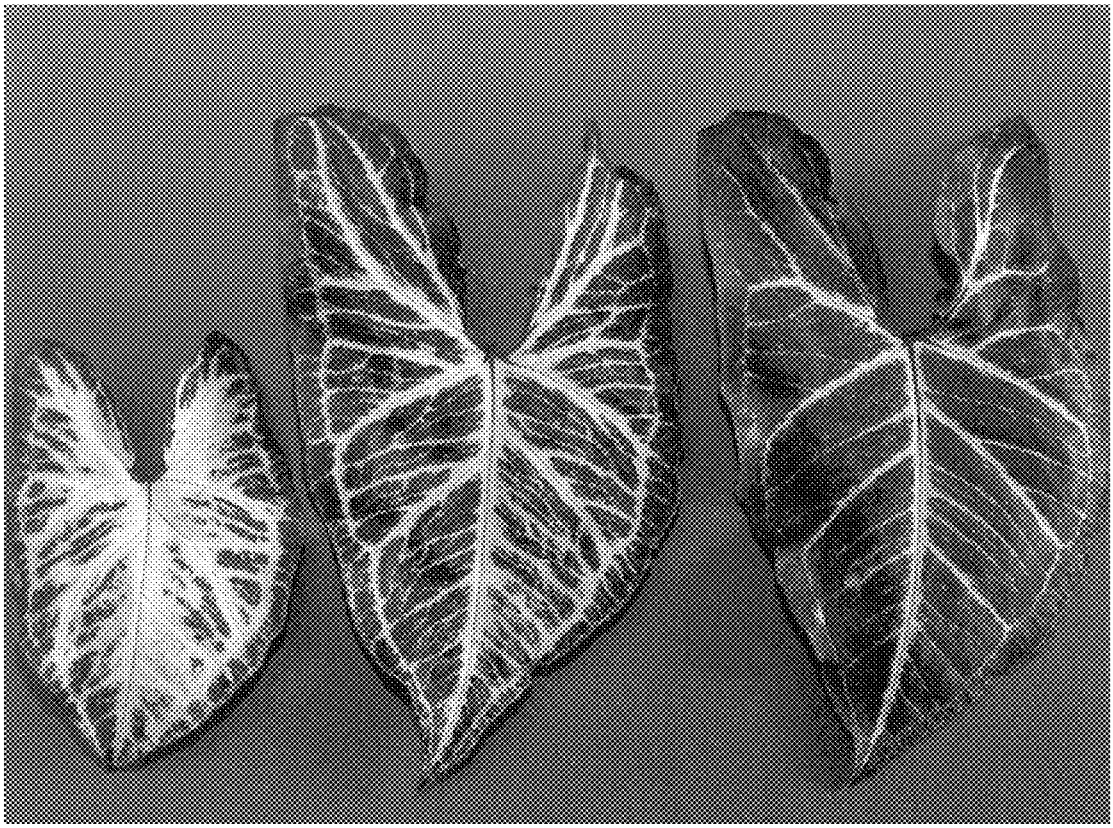

* * * * *